US011896243B2

(12) United States Patent
Aoude

(10) Patent No.: US 11,896,243 B2
(45) Date of Patent: Feb. 13, 2024

(54) SURGICAL TOOL GUIDE

(71) Applicant: Ahmed Aoude, Pointe-Claire (CA)

(72) Inventor: Ahmed Aoude, Pointe-Claire (CA)

( * ) Notice: Subject to any disclaimer, the term of this patent is extended or adjusted under 35 U.S.C. 154(b) by 576 days.

(21) Appl. No.: 17/055,688

(22) PCT Filed: May 16, 2019

(86) PCT No.: PCT/CA2019/050660
§ 371 (c)(1),
(2) Date: Nov. 16, 2020

(87) PCT Pub. No.: WO2019/218069
PCT Pub. Date: Nov. 21, 2019

(65) Prior Publication Data
US 2021/0186531 A1    Jun. 24, 2021

Related U.S. Application Data

(60) Provisional application No. 62/672,131, filed on May 16, 2018.

(51) Int. Cl.
*A61B 34/30*    (2016.01)
*A61B 17/17*    (2006.01)
(Continued)

(52) U.S. Cl.
CPC .......... *A61B 17/1757* (2013.01); *A61B 90/06* (2016.02); *A61B 90/11* (2016.02);
(Continued)

(58) Field of Classification Search
CPC ..... A61B 34/30; A61B 19/201; A61B 19/203; A61B 19/5244; A61B 17/17;
(Continued)

(56) References Cited

U.S. PATENT DOCUMENTS

| 4,784,126 A | * | 11/1988 | Hourahane | ............ A61B 17/29 606/329 |
| 4,922,897 A | * | 5/1990 | Sapega | .............. A61B 17/1764 606/916 |
| 5,163,940 A | | 11/1992 | Bourque | |

FOREIGN PATENT DOCUMENTS

| CN | 2680212 | 2/2005 |
| CN | 103040526 | 4/2013 |

(Continued)

*Primary Examiner* — Vi X Nguyen
(74) *Attorney, Agent, or Firm* — NORTON ROSE FULBRIGHT CANADA

(57) ABSTRACT

A surgical tool guide comprises an anchor body extending between a proximal end and a distal end along an anchor axis. The anchor body has a piercing element at the proximal end. An angle adjustor arcuately extends between two opposed ends. The angle adjustor is mounted to the anchor body between the proximal end and the distal end. A guide body is cannulated along a longitudinal length thereof to define a guide passage extending along a guide axis. The guide body is mounted to the angle adjustor such that the guide axis intersects the anchor axis at a target surgical point and an angle is defined between the anchor axis and the guide axis. The anchor body and/or the guide body is displaceable relative to the other along the angle adjustor to vary at least one of the angle and a depth of the target surgical point.

12 Claims, 8 Drawing Sheets

(51) Int. Cl.
*A61B 90/00* (2016.01)
*A61B 90/11* (2016.01)
*A61B 17/00* (2006.01)

(52) U.S. Cl.
CPC . *A61B 2017/0092* (2013.01); *A61B 2090/061* (2016.02); *A61B 2090/062* (2016.02); *A61B 2090/067* (2016.02); *A61B 2090/3966* (2016.02)

(58) Field of Classification Search
CPC ........ A61B 17/1757; A61B 2017/0092; A61B 90/06; A61B 90/11
See application file for complete search history.

(56) References Cited

FOREIGN PATENT DOCUMENTS

| | | |
|---|---|---|
| CN | 208096813 | 11/2018 |
| FR | 2901465 | 11/2007 |
| JP | 2012085998 | 5/2012 |

* cited by examiner

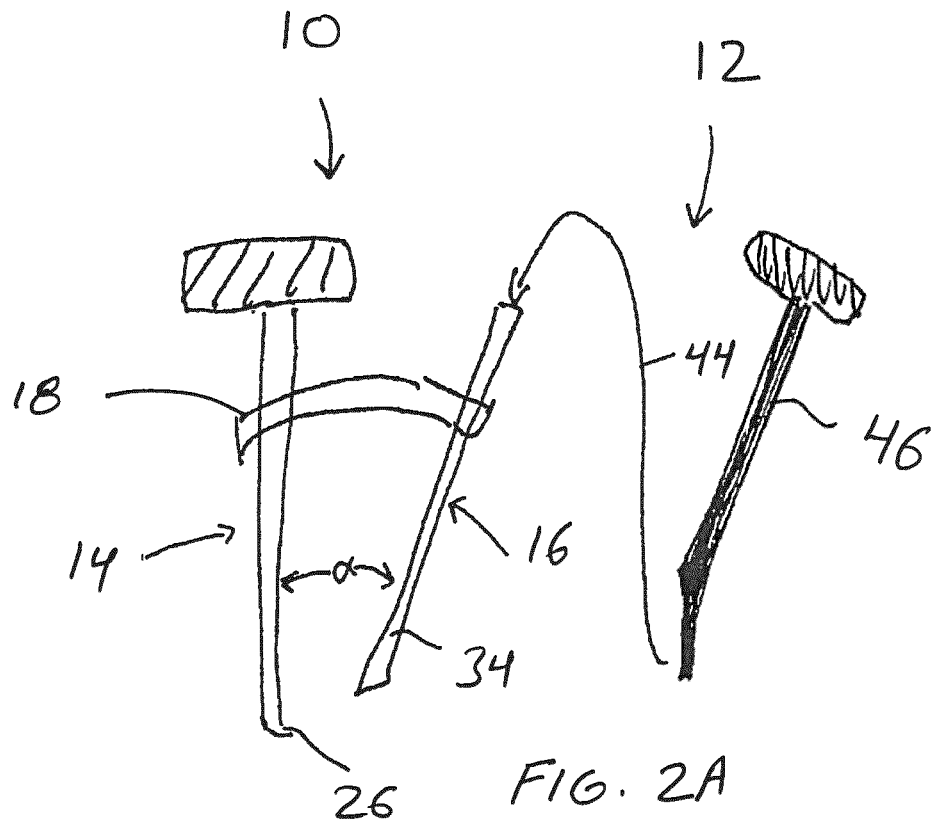
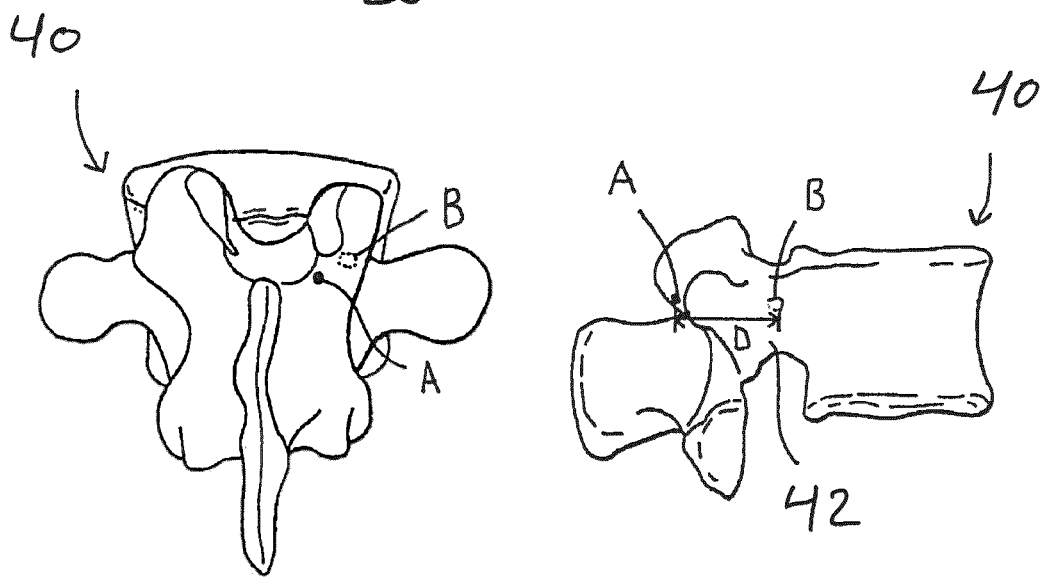
FIG. 2A
FIG. 2B
FIG. 2C

SURGICAL TOOL GUIDE

CROSS-REFERENCE TO RELATED APPLICATIONS

The present application is a national stale entry under 35 U.S.C. 371 of International Patent Application No. PCT/CA2019/050660 filed May 16, 2019, which claims priority on U.S. Patent Application No. 62/672,131 filed May 16, 2018, the entire contents of each of which is incorporated herein by reference.

TECHNICAL FIELD

The present disclosure relates generally to surgical devices and, more particularly, to a guide for use with a surgical tool.

BACKGROUND

Pedicle screws are a particular type of bone screw designed for implantation into a vertebral pedicle in the context of spine surgery. Such pedicle screws are used to correct deformities and/or to treat trauma. Similar to other bone screws, pedicle screws may be used in instrumentation procedures to affix rods and plates to the spine. Pedicle screw may also be used to immobilize part of the spine to assist fusion by holding bony structures together.

In order to position and insert pedicle screws in place, the surgeon typically uses fluoroscopy or x-ray imagery to determine the appropriate depth and angle for screw placement. The most commonly used technique for pedicle screw placement is a free-hand technique in which the surgeons uses their knowledge of anatomy, visual references, and feel to position and install a guide wire at the desired location and angle, and the guide wire is subsequently used to ensure that screws are correctly placed within vertebral pedicles. Alternative techniques include image guidance systems or computer-assisted surgery (CAS) system which, while often effective, are relative complex, have high associated costs, and require increased operation time.

The lack of adequate guidance for surgeons can in some situations cause screw misplacement. Misplacement of pedicle screws can cause a variety of problems, ranging from relatively minor issues such as weakness or sensory loss, to more major consequences such as paralysis.

SUMMARY OF THE INVENTION

There is accordingly provided a surgical tool guide comprising: an anchor body extending between a proximal end and a distal end along an anchor axis, the anchor body having a piercing element at the proximal end adapted to pierce bone tissue and to anchor the anchor body thereto; an angle adjustor including an arcuate body arcuately extending between two opposed ends, visual angle markings displayed on a surface of the arcuate body, the angle markings indicative of measured angles therebetween, the angle adjustor mounted to the anchor body between the proximal end and the distal end; a guide including a tubular body cannulated along a longitudinal length thereof to define a guide passage extending therethrough along a guide axis, the guide mounted to the angle adjustor such that the guide axis intersects the anchor axis at a target surgical point and an angle is defined between the anchor axis and the guide axis, the guide passage adapted to receive and guide a surgical tool therethrough; and at least one of the anchor body and the guide displaceable relative to the other along the angle adjustor to vary at least one of the angle and a depth of the target surgical point, the depth defined between the piercing element and the target surgical point along the anchor axis.

The surgical tool guide as defined herein may also include, in whole or in part, and in any combination, one or more of the following features.

At least one of the anchor body and the guide is displaceable relative to the angle adjustor in a corresponding direction along one of the anchor axis and the guide axis.

The anchor body includes length markings displayed on at least an outer surface portion of the anchor body, the outer surface portion intersecting the angle adjustor upon mounting the anchor body to the angle adjustor, the length markings indicative of measured lengths therebetween.

At least a portion of the anchor body is radiopaque such that said portion is impenetrable to X-rays.

The anchor body is made from a unitary corpus.

The anchor body includes at least one handle that is made from a radiolucent material.

The handle is disposed along the anchor axis at a distal end of the anchor body opposite the piercing element at the proximal end.

The at least one handle is disposed at a length perpendicular to the anchor axis.

The tubular body of the guide includes at least length markings displayed on an outer surface portion of the guide body, the outer surface portion intersecting the angle adjustor upon mounting the guide body to the angle adjustor, the length markings indicative of measured lengths therebetween.

The guide body includes a proximal outlet opening having a sharp edge adapted to engage and penetrate skin tissue.

The angle adjustor includes a base fixed to one end of the arcuate body, the defining a bore therethrough that receives a locating sleeve, the base being displaceable along the locating sleeve to vary a vertical position of the angle adjustor and thus the guide body mounted thereto.

The guide includes an adjustment block that is displaceable along the arcuate body of the adjustment mechanism, the adjustment block defining a bore therethrough receiving the tubular guide body.

There is also provided a surgical tool kit comprising: a surgical tool; an anchor body extending between a proximal end and a distal end along an anchor axis, the anchor body having a piercing element at the proximal end adapted to pierce bone tissue and to anchor the anchor body thereto; an angle adjustor arcuately extending between two opposed ends, the angle adjustor having visual angle markings displayed on a surface of the angle adjustor between the two opposed ends, the angle markings indicative of measured angles therebetween, the angle adjustor mounted to the anchor body between the proximal end and the distal end; a guide body cannulated along a longitudinal length thereof to define a guide passage extending therethrough along a guide axis, the guide body mounted to the angle adjustor such that the guide axis intersects the anchor axis at a target surgical point and an angle is defined between the anchor axis and the guide axis, the guide passage adapted to receive and guide a surgical tool therethrough; and at least one of the anchor body and the guide body displaceable relative to the other along the angle adjustor to vary at least one of the angle and a depth of the target surgical point, the depth defined between the piercing element and the target surgical point along the anchor axis.

The surgical tool kit as defined herein may also include, in whole or in part, and in any combination, one or more of the following features.

The surgical tool includes length markings displayed on at least an outer surface portion of the surgical tool, the length markings indicative of measured lengths therebetween.

At least one of the anchor body and the guide body is displaceable relative to the angle adjustor in a corresponding direction along one of the anchor axis and the guide axis.

The anchor body includes length markings displayed on at least an outer surface portion of the anchor body, the outer surface portion intersecting the angle adjustor upon mounting the anchor body to the angle adjustor, the length markings indicative of measured lengths therebetween.

At least a portion of the anchor body is radiopaque such that said portion is impenetrable to X-rays.

The anchor body includes at least one handle that is made from a radiolucent material.

The at least one handle is disposed along the anchor axis at a distal end of the anchor body opposite the piercing element at the proximal end.

The handle is disposed at a length perpendicular to the anchor axis.

The guide body includes at least length markings displayed on an outer surface portion of the guide body, the outer surface portion intersecting the angle adjustor upon mounting the guide body to the angle adjustor, the length markings indicative of measured lengths therebetween.

The guide body includes a proximal outlet opening having a sharp edge adapted to engage and penetrate skin tissue.

In another aspect, there is alternately provided a surgical tool guide comprising an anchor body extending between a proximal end and a distal end along an anchor axis, the anchor body having a piercing element at the proximal end adapted to pierce bone tissue and to anchor the anchor body thereto; an angle adjustor arcuately extending between two opposed ends, the angle adjustor having visual angle markings displayed on a surface of the angle adjustor between the two opposed ends, the angle markings indicative of measured angles therebetween, the angle adjustor mounted to the anchor body between the proximal end and the distal end; a guide body cannulated along a longitudinal length thereof to define a guide passage extending therethrough along a guide axis, the guide body mounted to the angle adjustor such that the guide axis intersects the anchor axis at a target surgical point and an angle is defined between the anchor axis and the guide axis, the guide passage adapted to receive and guide a surgical tool therethrough; and at least one of the anchor body and the guide body displaceable relative to the other along the angle adjustor to vary at least one of the angle and a depth of the target surgical point, the depth defined between the piercing element and the target surgical point along the anchor axis.

In yet another aspect, there is alternately provided a surgical tool kit comprising a surgical tool; an anchor body extending between a proximal end and a distal end along an anchor axis, the anchor body having a piercing element at the proximal end adapted to pierce bone tissue and to anchor the anchor body thereto; an angle adjustor arcuately extending between two opposed ends, the angle adjustor having visual angle markings displayed on a surface of the angle adjustor between the two opposed ends, the angle markings indicative of measured angles therebetween, the angle adjustor mounted to the anchor body between the proximal end and the distal end; a guide body cannulated along a longitudinal length thereof to define a guide passage extending therethrough along a guide axis, the guide body mounted to the angle adjustor such that the guide axis intersects the anchor axis at a target surgical point and an angle is defined between the anchor axis and the guide axis, the guide passage adapted to receive and guide a surgical tool therethrough; and at least one of the anchor body and the guide body displaceable relative to the other along the angle adjustor to vary at least one of the angle and a depth of the target surgical point, the depth defined between the piercing element and the target surgical point along the anchor axis.

BRIEF DESCRIPTION OF THE DRAWINGS

Reference is now made to the accompanying figures in which:

FIG. 2A is a schematic side view of the surgical tool guide of FIG. 1 and a surgical tool used in connection therewith;

FIG. 2B is a posterior elevational view of a vertebrae showing insertion and target points relevant to the surgical tool guide of FIG. 1;

FIG. 2C is a side elevational view of the vertebrae of FIG. 2B;

DETAILED DESCRIPTION

Figure 1:
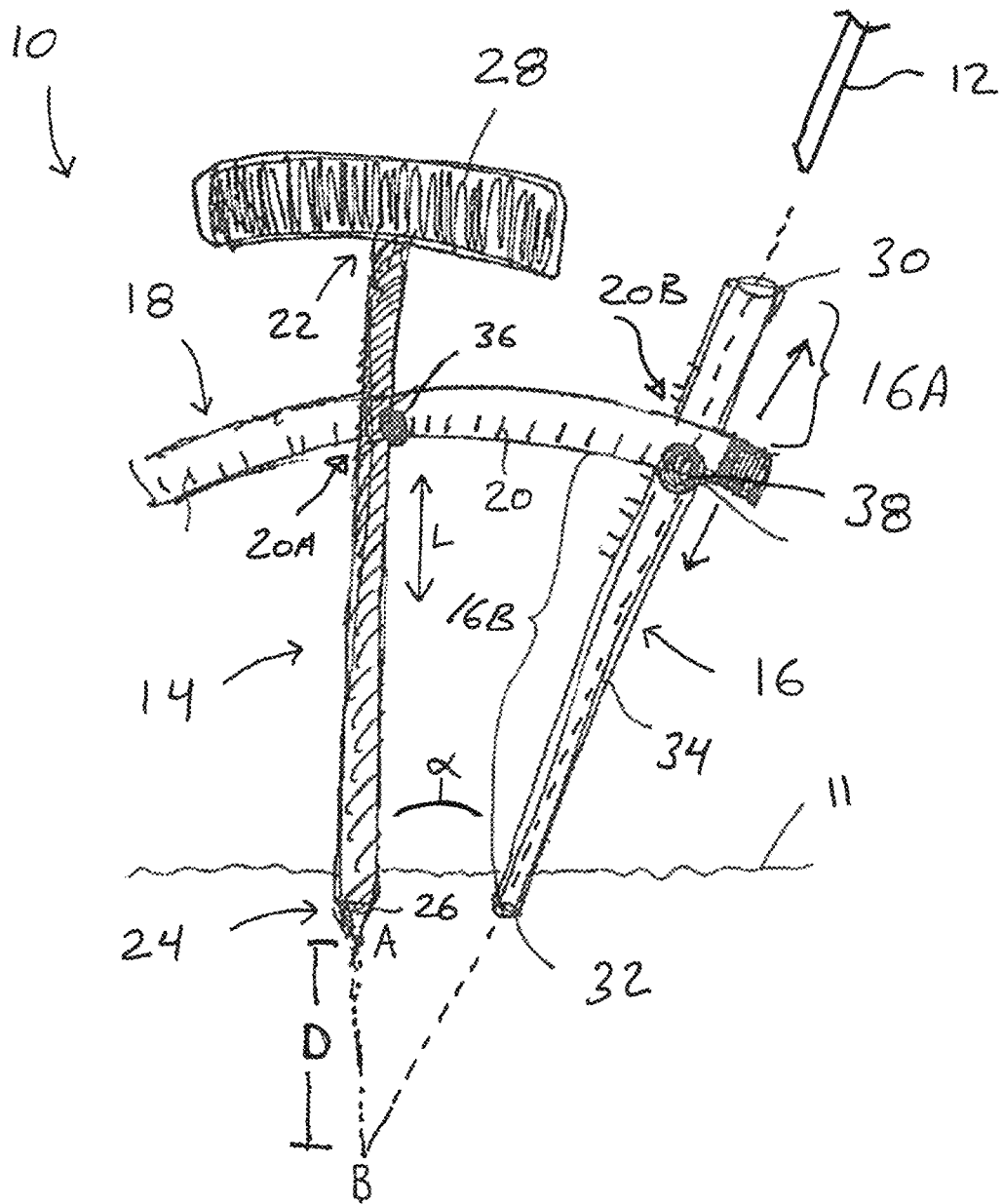
FIG. 1 is a side view of a surgical tool guide of the present disclosure.

FIG. 1 illustrates a surgical tool guide 10 for guiding a surgical tool 12 during surgery or other medical procedures. The tool guide 10 can allow a health professional, such as a surgeon, to improve the accuracy of placement and positioning of the surgical tool 12 relative to a tissue 11 of a patient. The tissue 11 of the patient may refer to a bone tissue of the patient. More particularly, the tool guide 10 may allow the surgeon to make incremental and quantifiable adjustments in the position of the surgical tool 12, which allows the surgeon to fine tune a trajectory of the surgical tool 12 intra-operatively in order to obtain the correct placement of the surgical tool 12 relative to the patient's tissue 11. This may contribute to reducing the amount of trial-and-error that a surgeon needs to perform in order to find the correct trajectory of the surgical tool 12, which can help to improve safety and reduce the duration of surgical operations. The tool guide 10 may be particularly suited for those surgical operations during which the surgeon employs "free hand" techniques.

The tool guide 10 is described herein in the context of spinal surgery, and more particularly, in the context of implanting guide wires, pedicle screws, or both, into vertebral pedicles. Similarly, the surgical tool 12 is described as being one commonly used for such spinal surgeries, and can be any one of a guide wire, an awl, a feeler, a Jamshidi™ needle, and a pedicle screw. However, the tool guide 10 can also be used during surgery on other parts of the body, and the present disclosure does not limit it to being used only during spinal surgery. Similarly, the surgical tool 12 is not limited to being a spinal surgery tool. Various types of other surgical devices and tools are therefore within the scope of the present disclosure depending on the surgical operation being performed. For example, the tool guide 10 may be used in anesthetic procedures, nerve block and catheter placement pre-op or post-op using ultrasound, and the like.

As will be discussed in greater detail herein, the tool guide 10 can be used with intra-operative image, typically X-ray imaging or fluoroscopy, to further assist the surgeon in guiding the surgical tool 12. Depending on the surgical procedure and the material from which the tool guide 10 is made, the tool guide 10 can be adapted for one-time use, or can be autoclaved for sterilisation, and therefore, repeated use.

The tool guide 10 has an anchor body 14 to support and/or stabilize the tool guide 10 relative to the tissue 11, a guide body 16 to guide the surgical tool 12 toward the tissue 11 and an angle adjustor 18 to adjust an angle between the anchor body 14 and the guide body 16.

The angle adjustor 18 is curved in the shape of an arch (i.e. it is arcuate) along its length between its opposed ends. As will be explained in more detail below, the angle adjustor 18 helps to determine and/or adjust an angle α between the anchor body 14 and the guide body 16. For example, the angle adjustor 18 therefore has visually-observable angle markings 20 that are displayed on one of the exposed surfaces of the angle adjustor 18 so that the surgeon or the medical professional can adjust and/or determine the angle α. The angle markings 20 can indicate measured angles therebetween. Examples of angle markings 20 include numerical angle values, colour schemes, gradations, or other visual indicia that are indicative of the angle α. For example, the angle markings 20 can be displayed similar to markings on a protractor. In other words, the angle adjustor 18 can be used in a similar way as the protractor such that a first reference is specified, and a second reference can be determined at an angle relative to the first reference to adjust the angle between the first reference and the second reference. Each angle marking 20 may define a corresponding direction extending radially toward a center of the angle adjustor 18. The corresponding direction is intended to indicate a ray, also known as a side of the angle, which can be used to form an angle defined by two rays lying in a plane. The corresponding direction may be illustrated as a line or otherwise on the angle adjustor 18 to indicate the side of the angle α. In an alternate embodiment, the tool guide 10 includes an electronic display to visually display the value for the angle α. This display may be integrated into the tool guide 10, or may be removably attached thereto. In yet another alternate embodiment, an accelerometer is used to determine the angle α, which may also be in communication with the visual display for the purposes of displaying the angle as determined by the accelerometer.

The anchor body 14 may be mounted to the angle adjustor 18 at any selected point thereon. For example, the anchor body 14 may be mounted at a first angle marking 20A of the angle markings 20. The anchor body 14 is elongated between two opposed outer distal end 22 and inner proximal end 24 along an anchor axis 14A. In use, when the anchor body 14 is mounted to the angle adjustor 18, the anchor body 14 is elongated along the corresponding direction of the first angle marking 20A. As such, the anchor body 14 forms the first side of the angle α. The anchor body 14 may be made from a unitary corpus. In the depicted embodiment of FIG. 1, the anchor body 14 is mounted to the angle adjustor 18 such that the opposed outer distal end 22 and the inner proximal end 24 of the anchor body 14 are on opposed sides of the angle adjustor 18.

The inner proximal end 24 has a piercing element 26 that is used to pierce the tissue 11 of the patient. For example, the piercing element 26 may be used to pierce a cortical bone tissue of a vertebra to anchor the anchor body 14 to the vertebrae at an anchor point A. The piercing element 26 is radiopaque so that it at least partially obstructs the passage of radiant energy, such as X-rays, and thus remains visible during intraoperative imaging. Alternately, at least a portion of the anchor body 14, in addition to the piercing element 26, may be radiopaque. The term radiopaque may also refer to a state of being impenetrable to X-rays and other radiation.

The anchor body 14 is solid throughout at last a majority of its longitudinal extent, in that it is not cannulated and is not intended to receive a guide wire or a surgical tool therethrough.

In the embodiment shown in FIG. 1, the anchor body 14 may be manipulated by the medical professional to be anchored within cortical bone tissue of the vertebrae at the anchor point A. The anchor body 14 can therefore include any accessories that facilitate this functionality. In the depicted embodiment of FIG. 1, for example, the anchor body 14 has a handle 28 located at the outer distal end 22 of the anchor body 14 to facilitate manipulation of the anchor body 14 and the tool guide 10, by the medical professional. The handle 28 may be made from a radiolucent material that is relatively penetrable by X-rays or other forms of radiation. The term radiolucent material is intended to refer a material that is at least more penetrable than a substantially radiopaque metal or metal alloy. The term radiolucent may also refer to a state of being transparent to X-rays.

The guide body 16 may be mounted to the angle adjustor 18 at any suitable point thereon. For example, the guide body 16 may be mounted at a second angle marking 20B of the angle markings 20. The guide body 16 is elongated between two opposed distal inlet aperture 30 and proximal exit aperture 32 along a guide axis 14B. In use, when the guide body 16 is mounted to the angle adjustor 18, the guide body 16 is elongated along the corresponding direction of the second angle marking 20B. As such, the guide body 16 forms the second side of the angle α.

Unlike the solid anchor body 14, the guide body 16 is cannulated and thus defines a hollow interior passage that extends along at least some of its length (and in one particular embodiment, its entire longitudinal extent) to guide the surgical tool 12 to a target surgical area or point B in the vertebrae. The point B may indicate the center of the angle adjustor 18. The guide body 16 defines an internal and closed perimeter guide passage 34, which extends through the guide body 16 between distal inlet aperture 30 and the proximal exit aperture 32, which may be positioned within the tissue 11 of the patient during use of the tool guide 10. In use, the guide passage 34 may extend along the corresponding direction of the second angle marking 20B. As will be explained in greater detail below, the guide passage 34 is positioned and sized to receive the surgical tool 12 therein via the inlet aperture 30 and to guide the surgical tool 12 through the guide body 16 to exit therefrom at the exit aperture 32.

In use, the angle adjustor 18 may divide the guide body 16 between a first length 16A and a second length 16B. The first and second lengths 16A, 16B are lengths of the guide body 16 above and below, respectively, the angle adjustor 18. The first and second lengths 16A, 16B may be adjusted by displacing the guide body 16 relative to the angle adjustor 18 in the corresponding direction of the second angle marking 20B. Stated differently, the guide body 16 is displaceable along its longitudinal axis so as to adjust the distance of the guide body 16 relative to the target surgical point B in the vertebrae.

In the depicted embodiment, the angle adjustor 18 and the guide body 16 mounted thereto are displaceable along direction L relative to the anchor body 14. The anchor body 14 may have a locking mechanism 36 to allow and arrest displacement of the angle adjustor 18 along an axis of the anchor body 14. More particularly, the angle adjustor 18 and the guide body 16 mounted thereto are displaceable in the direction L parallel to the axis of the anchor body 14 towards and away from the target surgical point B. In the embodiment shown, the direction L is the same as the corresponding direction of the first angle marking 20A. By displacing the angle adjustor 18 and the guide body 16 in this manner, the medical professional is able to vary the distance D between the anchor point A and the target surgical point B.

One or both of the anchor body 14 and the guide body 16 are displaceable relative to the other along the angle adjustor 18 to adjust the angle α between the anchor body 14 and the guide body 16. Stated differently, one or both of the anchor body 14 and the guide body 16 may be slidingly displaced along the angle adjustor 18 toward and away from one another to adjust the angle α measured between them. The angle α can have any suitable range. For example, the angle α can range between 0° and 45° degrees. The guide body 16 may also have a locking mechanism 38 to allow and arrest displacement of the guide body 16 along the angle adjustor 18. For example, the anchor body 14 may be positioned at the first angle marking 20A indicating 0 degrees. The guide body 16 may be positioned at the second angle marking 20B indicating 20 degrees if the medical professional has determined that the angle α is 20 degrees. Stated differently, the anchor body 14 and the guide body 16 are positioned to adjust the angle α therebetween.

The use of two relatively thin devices, the anchor body 14 and the guide body 16, may limit the size of the surgical incision needed to effect the surgical operation of the vertebrae. Indeed, the size of the surgical incision can be limited to the area defined by the circumference of the anchor body 14 and the guide body 16.

Referring to FIGS. 2A to 2C, the use of the tool guide 10 will be described. In operation, an appropriate incision in the skin of the patient is made, and the anchor body 14 is inserted through the incision until the piercing element penetrates into the cortical bone tissue of the vertebrae 40 to anchor the tool guide 10 at the anchor point A. In the depicted embodiment, the medical professional attempts to anchor the anchor body 14 at a center of the pedicle 42, as viewed in an anterior-posterior radiographic image (i.e. in the coronal plane), as shown in FIG. 2C.

A distance D from the anchor point A to the target surgical point B in the pedicle is then determined. This projection distance D is a measure of a depth into the vertebrae 40 to the target surgical point B. In the depicted embodiment, the distance D is determined from intraoperative radiographic images, such as the image of the vertebrae in the sagittal plane shown in FIG. 2C. The distance D may also be determined pre-operatively using X-rays, CT scans, MRI scans, and the like. As can be seen, the anchor point A is spaced from the target surgical point B by the distance D. In an alternate embodiment, the medical professional supplies the distance D from the known geometry of the vertebrae 40. For example, it is known that the size of the average pedicle is about 20 mm.

The guide body 16 is then positioned relative to the anchor body 14 as a function of the distance D to the target surgical point B in the pedicle. When the distance D is known, the appropriate angle α can be determined. For example, using trigonometry based on the known lengths of the guide body 16, and the known length of the anchor body 14 plus distance D, the angle α is determinable. The angle α defines the orientation along which the surgical tool 12 will be inserted.

The surgical tool 12 is then inserted through the hollow guide body 16 to penetrate into the vertebrae 40 to the target surgical point B within the pedicle. In the depicted embodiment, the surgical tool 12 includes a guide wire 44 coupled to a handle 46. The handle 46 is manipulated by the medical professional to insert the guide wire 44 through the guide passage 34 of the guide body 16 to perforate the cortex bone tissue in proximity to the target surgical point B. The surgical tool 12 can include other devices as well, such as a pedicle screw.

Figure 3A:
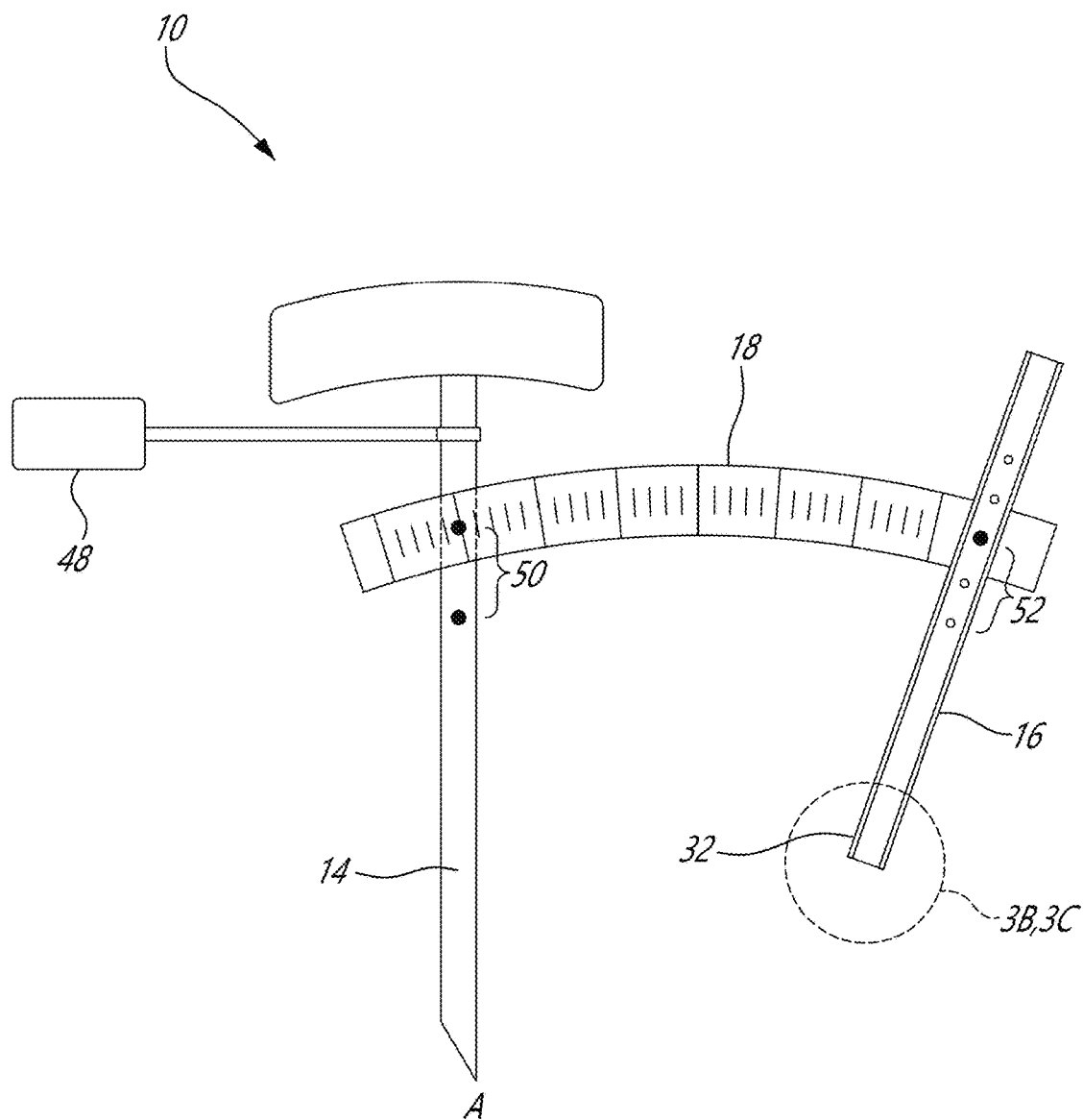
FIG. 3A is a side elevational view of the surgical tool guide of FIG. 1 having an additional handle.

Referring to FIG. 3A, another handle 48 is shown attached to the anchor body 14. The handle 48 may be used by the medical professional to manipulate the anchor body 14, the tool guide 10, or both, while keeping the hand of the medical professional away from X-rays or other radiation. The handle 48 is removably attached to the anchor body 14 at a distance along a length perpendicular to the anchor body 14. The distance may depend on the configuration of the tool guide 10 and location and strength of the X-rays.

The anchor body 14 includes length markings 50 on an outer surface thereof or on a portion of the outer surface. The length markings 50 are disposed on the outer surface that would intersect the angle adjustor 18 when the anchor body 14 is mounted to the angle adjustor 18. The length markings 50 indicate measured lengths between them. The length markings 50 may be used to adjust the displacement of the anchor body 14 relative to the angle adjustor 18.

The guide body 16 includes length markings 52 on an outer surface thereof or on a portion of the outer surface. The length markings 52 are disposed on the outer surface that would intersect the angle adjustor 18 when the guide body 16 is mounted to the angle adjustor 18. The length markings 52 indicate measured lengths between them. The length markings 52 may be used to adjust the displacement of the guide body 16 relative to the angle adjustor 18.

Figure 3B:
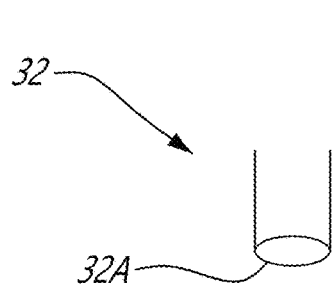
FIG. 3B is perspective view of an exit aperture of the surgical guide of FIG. 1 according to an embodiment.
Figure 3C:
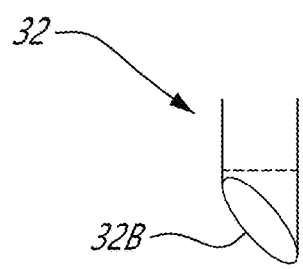
FIG. 3C is perspective view of the exit aperture of the surgical guide of FIG. 1 according to another embodiment.

Referring to FIGS. 3B-3C, examples of the exit aperture 32 or outlet opening are shown. FIG. 3B illustrates a blunt edge 32A of the exit aperture 32 and FIG. 3C illustrates a sharp edge 32B of the exit aperture 32. The sharp edge 32B may be adapted to engage and penetrate the skin tissue 11 of the patient. In some embodiments, the exit aperture 32 may have a retractable sharp edge 32B which can retract and extend beyond the blunt edge 32A. The guide body 16 may include a spring-loaded mechanism to retract and extend the sharp edge 32B.

Figure 4:
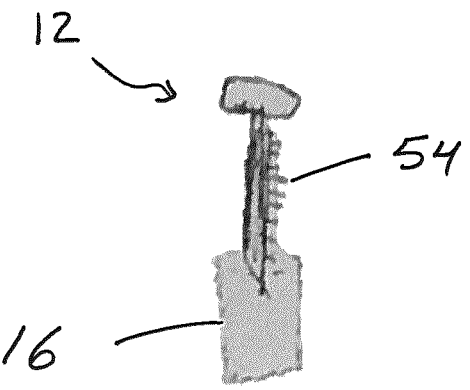
FIG. 4 is a schematic side view of a surgical tool.

Referring to FIG. 4, the surgical tool 12 is shown. The surgical tool 12 may form part of a surgical tool kit that includes the tool guide 10 and the surgical tool 12. The surgical tool 12 may include pins 54 extending perpendicularly relative to the surgical tool 12. The pins 54 are adapted to engage the guide body 16 to provide stopping positions between the surgical tool 12 and the guide body 16. The pins 54 may also determine a depth of the surgical tool 12 relative to the guide body 16. For example, the pins 54 may be marked to reveal a length of the surgical tool 12. In use, the surgical tool 12 may be positioned such that a pin 54 indicating the desired length or depth of the surgical tool 12 into the guide body 16 is engaged with a reference position of the guide body 16.

The surgical tool 12 may also include length markings on an outer surface thereof or on a portion of the outer surface. The length markings are disposed on the outer surface that would intersect the reference position when the surgical tool is inserted into the guide body 16. The length markings indicate measured lengths between them. The length markings may be used to adjust the displacement of the surgical tool relative to the guide body 16.

Figure 5:
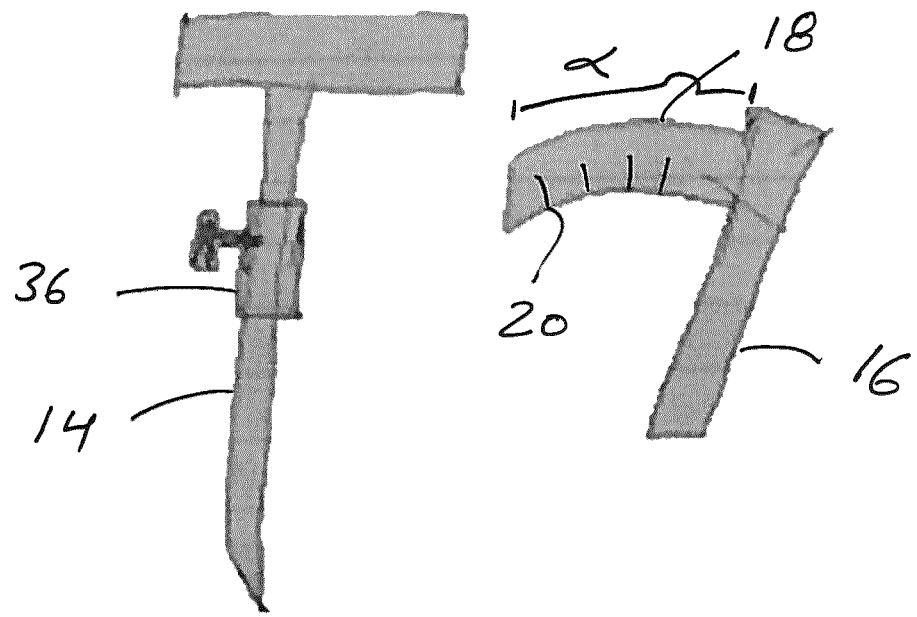
FIG. 5 is a side elevational view of a surgical tool guide, according to another embodiment.

Referring to FIG. 5, another embodiment of the surgical tool guide 100 is shown. The guide tool 100 is similar to the guide tool 10 described above. In the embodiment shown in FIG. 5, the guide body 16 is fixed to the angle adjustor 18 at one of the angle markings 20. The surgical tool 100 may have multiple combined angle adjustor 18 and guide body 16 fixed at different angles. For example, a first guide body 16 may be mounted to a corresponding angle adjustor 18 at an angle marking of 30 degrees and a second guide body 16 may be mounted to a corresponding angle adjustor 18 at an angle marking of 45 degrees. In use, the anchor body 14 can be mounted to one of the combined guide body 16 and angle adjustor 18 to adjust the angle α between the anchor body 14 and the guide body 16.

Figure 6A:
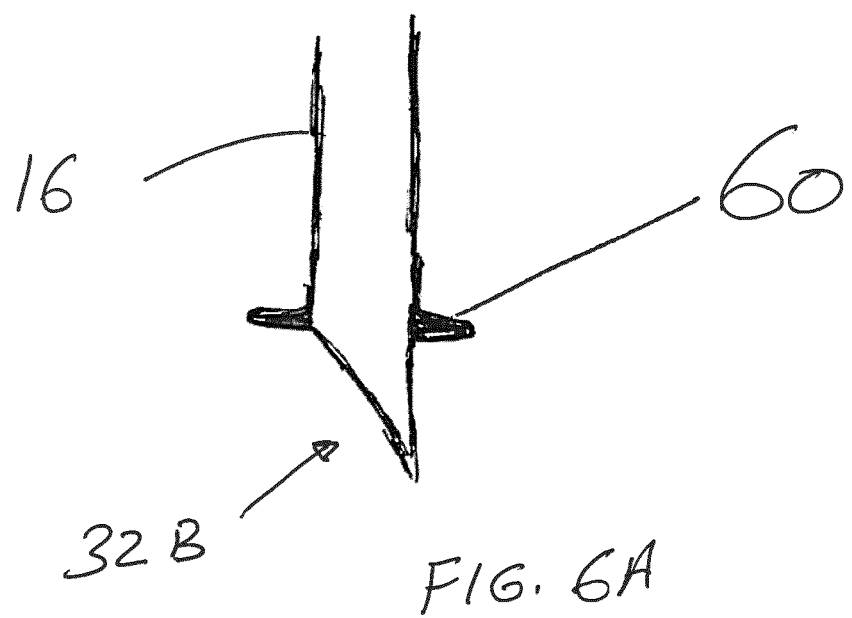
FIG. 6A is a side elevational view of the exit aperture of FIG. 3B, according to some embodiments.
Figure 6B:
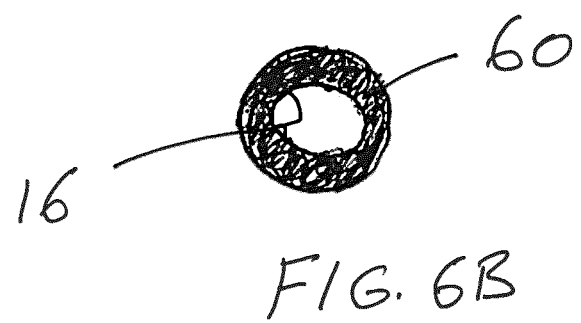
FIG. 6B is a top elevational view of the exit aperture of FIG. 6A.

Referring to FIGS. 6A and 6B, a bumper 60 is shown attached to the guide body 16 between the inlet aperture 30 and the exit aperture 32, 32A, 32B. The bumper 60 may have any suitable shape and made from any suitable material to arrest the guide body 16 on the tissue of the patient. As such, the bumper 60 may prevent plunging the sharp edge 32B excessively into the tissue of the patient. The bumper 60 is shown as a circumferential protrusion extending radially outward from the guide body 16. In some embodiments, the bumper 60 may be integrally formed with the guide body 16. In other embodiments, the bumper 60 is securely mountable to the guide body 16. The location of the bumper 60 on the guide body 16 may depend upon the anatomy of the patient.

In light of the preceding, the tool guide 10, 100 disclosed herein may improve the accuracy of surgical tool placement, such as pedicle screw placement in spine surgery. The tool guide 10, 100 can improve the "free hand" technique employed by surgeons for some procedures, and may contribute to reducing the number of X-ray images that need to be generated, thereby reducing exposure to radiation. The tool guide 10, 100 helps to obtain more precise movement modifications to the trajectory of the tool.

In comparison to CAS or image-guidance techniques, the tool guide 10, 100 can be cost effective, much less time consuming, and simpler to use. The tool guide 10, 100 provides, for example, guide wire for pedicle screw placement in a quick and safe manner. It is expected that increasing screw placement accuracy improves the outcomes of surgical procedures. The tool guide 10, 100 may be used in spinal surgery, and form part of a pedicle screw placement kit.

Figure 7:
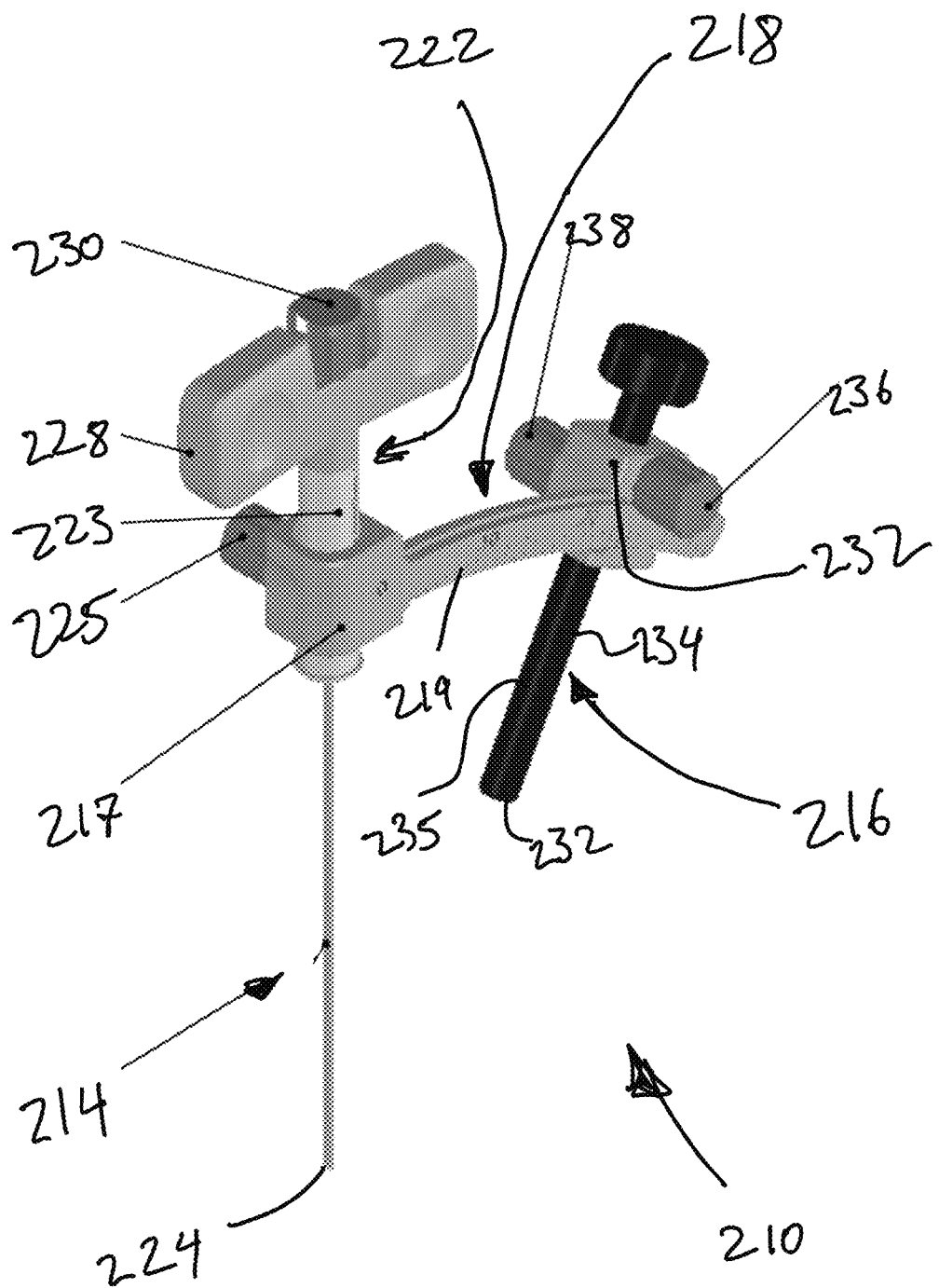
FIG. 7 is a perspective view of a surgical tool guide of the present disclosure.
Figure 8:
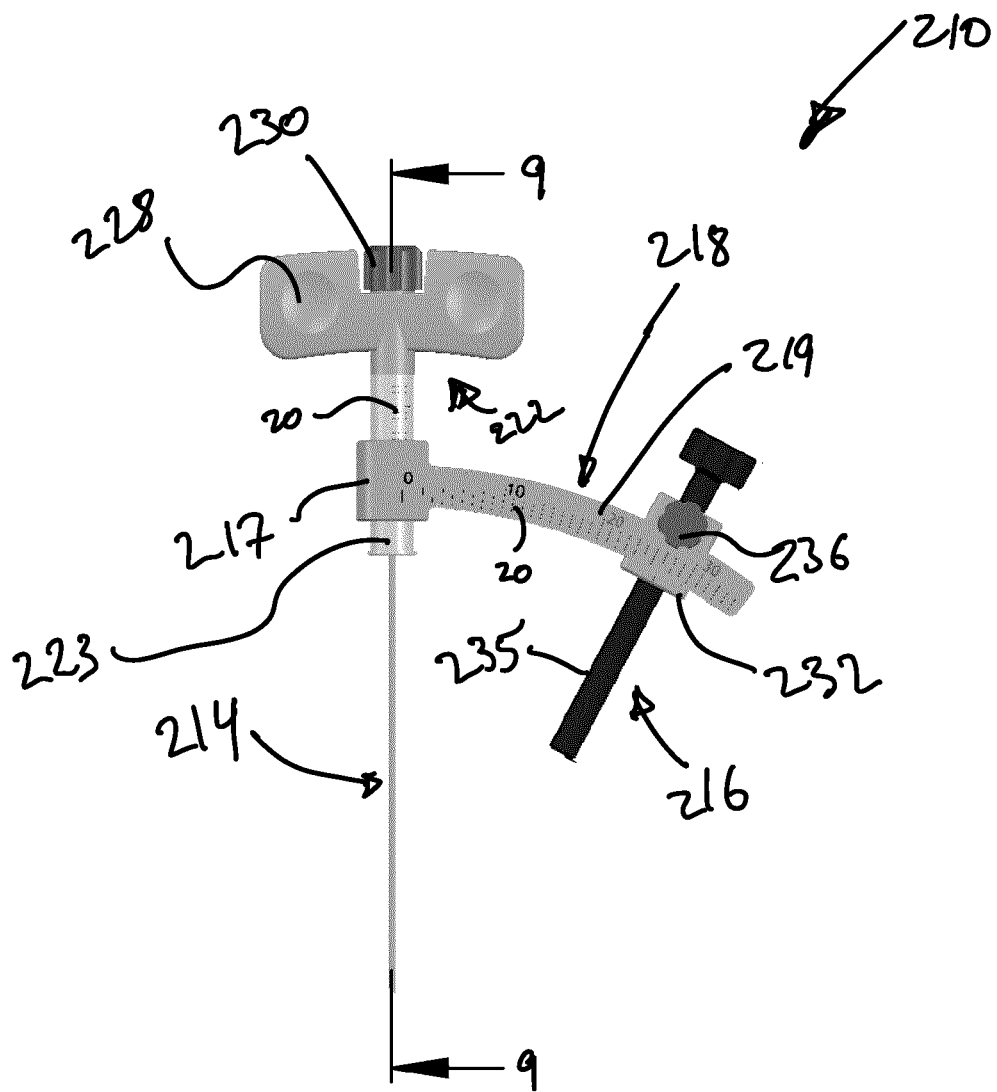
FIG. 8 is a side elevational view of the surgical tool guide of FIG. 7.
Figure 9:
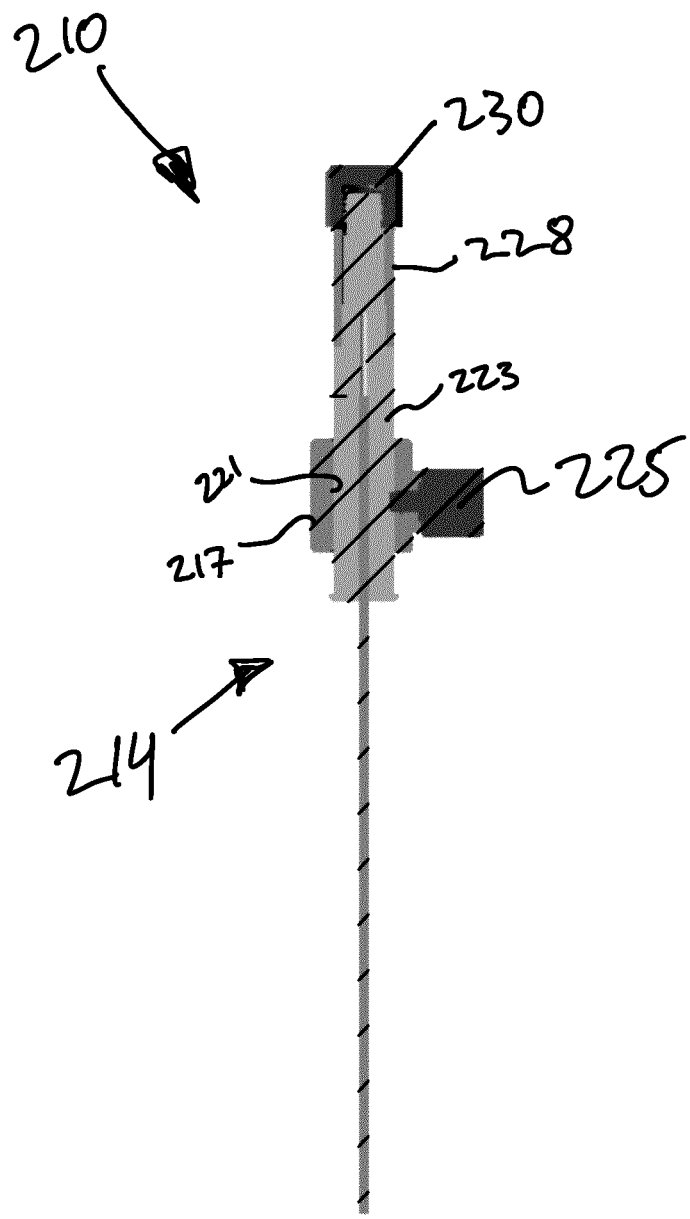
FIG. 9 is a cross-sectional view taken through line 9-9 in FIG. 8.

Referring now to FIGS. 7-9, a surgical tool guide 210 is depicted. The surgical tool guide 200 operates in a similar manner to the surgical tool guide 10 as described above, and therefore will only be described generally, with a focus on any elements thereof that may differ from the guides already described herein.

The surgical tool guide 210 includes generally an anchor body 214 used to locate, support and/or stabilize the tool guide 210 relative to the patient tissue 11, a guide body 216 which is used to guide the surgical tool 12 towards the tissue 11, and an angular adjustment mechanism 218 which is used to adjust the angle α (see FIG. 1) between the anchor body 214 and the guide body 216, as described above.

The angular adjustment mechanism 218 includes an arcuate body 219 that is fixed relative to a base 217 which secured to the anchor body 214. A central bore 221 (see FIG. 9) extends vertically through this base 217 and receives a locating sleeve 223 therein. The locating sleeve 223 and the base 217 are displaceable relative to each other, such that the base can be slide vertically along the locating sleeve 223 to vary the vertical position of the base 217 and thus the entire angular adjustment mechanism 18. A locking nut 225 is used to secure the base 217 in the desired location on the locating sleeve 223. As such, the vertical position of the entire angular adjustment mechanism 218 can be adjusted, and secured in a desired position.

Much as per the embodiment of FIG. 1, the anchor body 214 includes a handle 228 located at the outer distal end 222 of the anchor body 214 to facilitate manipulation of the anchor body 214 and the tool guide 210. In this embodiment, a needle and/or guidewire may also be inserted through the anchor body 214, and can be secured in place with an outer locking nut 230.

As best seen in FIG. 8, the outer surfaces of both the adjustment sleeve 223 and the arcuate body 219 of the adjustment mechanism include visually-observable markings 20 thereon, so that the surgeon or medical professional can see, adjust and/or measure the relative position and orientation of the guide body 16 and thus the surgical tool 12 guided thereby.

The guide body 216 includes a tubular body 235, that defines the closed perimeter bore therethrough for receiving the surgical tool 12. The hollow tubular body 235 is received within a displaceable adjustment block 232 (hereinafter, simply "block" 232) that is mounted to the guide body 216 of the adjustment mechanism for relative sliding displacement therealong. The angular position of the guide body 216 relative to the anchor body 214 can therefore be adjusted by sliding the block 232 along the arcuate body 219 of the adjustment mechanism 218, thereby changing the relative angular position of the tubular body 235 relative to the vertical reference defined by the anchor body 214 (i.e. thereby modify angle α (see FIG. 1). Once the desired angle is reached, the block 232 is locked in position by tightening the locking nut 236, which secures the block 232 in place on the arcuate body 219 and thus prevents any further relative movement therebetween.

If necessary, the vertical position of the tubular body 235 can also be adjusted, without changing the desired angle α between the tubular body 235 of the guide body 216 and the anchor body 214. The tubular body 235 of the guide body 216 can be slid axially within the bore defined in the block 232, and locked in place using the further adjustment nut 238.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure, and such modifications are intended to fall within the appended claims.

The invention claimed is:

1. A surgical tool guide comprising:
an anchor body extending between a proximal end and a distal end along an anchor axis, the anchor body having a piercing element at the proximal end adapted to pierce bone tissue and to anchor the anchor body thereto;
an angle adjustor including an arcuate body arcuately extending between two opposed ends, visual angle markings displayed on a surface of the arcuate body, the angle markings indicative of measured angles therebetween, the angle adjustor mounted to the anchor body between the proximal end and the distal end;
a guide including a tubular body cannulated along a longitudinal length thereof to define a guide passage extending therethrough along a guide axis, the guide mounted to the angle adjustor such that the guide axis intersects the anchor axis at a target surgical point and an angle is defined between the anchor axis and the guide axis, the guide passage adapted to receive and guide a surgical tool therethrough; and
at least one of the anchor body and the guide displaceable relative to the other along the angle adjustor to vary at least one of the angle and a depth of the target surgical point, the depth defined between the piercing element and the target surgical point along the anchor axis.

2. The surgical tool guide as defined in claim 1, wherein at least one of the anchor body and the guide is displaceable relative to the angle adjustor in a corresponding direction along one of the anchor axis and the guide axis.

3. The surgical tool guide as defined in claim 1, wherein the anchor body includes length markings displayed on at least an outer surface portion of the anchor body, the outer surface portion intersecting the angle adjustor upon mounting the anchor body to the angle adjustor, the length markings indicative of measured lengths therebetween.

4. The surgical tool guide as defined in claim 1, wherein at least a portion of the anchor body is radiopaque such that said portion is impenetrable to X-rays.

5. The surgical tool guide as defined in claim 1, wherein the anchor body is made from a unitary corpus.

6. The surgical tool guide as defined in claim 1, wherein the anchor body includes at least one handle that is made from a radiolucent material.

7. The surgical tool guide as defined in claim 6, wherein the at least one handle is disposed along the anchor axis at a distal end of the anchor body opposite the piercing element at the proximal end.

8. The surgical tool guide as defined in claim 6, wherein the at least one handle is disposed at a length perpendicular to the anchor axis.

9. The surgical tool guide as defined in claim 1, wherein the tubular body of the guide includes at least length markings displayed on an outer surface portion of the guide body, the outer surface portion intersecting the angle adjustor upon mounting the guide body to the angle adjustor, the length markings indicative of measured lengths therebetween.

10. The surgical tool guide as defined in claim 1, wherein the guide body includes a proximal outlet opening having a sharp edge adapted to engage and penetrate skin tissue.

11. The surgical tool guide as defined in claim 1, wherein the angle adjustor includes a base fixed to one end of the arcuate body, the defining a bore therethrough that receives a locating sleeve, the base being displaceable along the locating sleeve to vary a vertical position of the angle adjustor and thus the guide body mounted thereto.

12. The surgical tool guide as defined in claim 11, wherein the guide includes an adjustment block that is displaceable along the arcuate body of the adjustment mechanism, the adjustment block defining a bore therethrough receiving the tubular guide body.

* * * * *